(12) United States Patent
Tao et al.

(10) Patent No.: US 11,860,051 B2
(45) Date of Patent: Jan. 2, 2024

(54) INTELLIGENT BIONIC HUMAN BODY PART MODEL DETECTION DEVICE AND METHOD FOR MANUFACTURING SAME

(71) Applicant: The Hong Kong Research Institute of Textiles and Apparel Limited, Hong Kong (CN)

(72) Inventors: Xiao-ming Tao, Hong Kong (CN); Bao Yang, Hong Kong (CN); Xi Wang, Hong Kong (CN); Su Liu, Hong Kong (CN); Xia Guo, Hong Kong (CN); Shi-rui Liu, Hong Kong (CN)

(73) Assignee: THE HONG KONG RESEARCH INSTITUTE OF TEXTILES AND APPAREL LIMITED, Hong Kong (CN)

( * ) Notice: Subject to any disclaimer, the term of this patent is extended or adjusted under 35 U.S.C. 154(b) by 630 days.

(21) Appl. No.: 17/040,229

(22) PCT Filed: Mar. 29, 2018

(86) PCT No.: PCT/CN2018/081017
§ 371 (c)(1),
(2) Date: Sep. 22, 2020

(87) PCT Pub. No.: WO2019/178886
PCT Pub. Date: Sep. 26, 2019

(65) Prior Publication Data
US 2021/0010877 A1    Jan. 14, 2021

(30) Foreign Application Priority Data
Mar. 22, 2018 (CN) .......................... 201810249322.8

(51) Int. Cl.
*G01L 1/24* (2006.01)
*G06T 7/62* (2017.01)
*G02B 6/02* (2006.01)

(52) U.S. Cl.
CPC .......... *G01L 1/246* (2013.01); *G02B 6/02076* (2013.01); *G06T 7/62* (2017.01); *G06T 2200/04* (2013.01); *G06T 2207/30196* (2013.01)

(58) Field of Classification Search
None
See application file for complete search history.

(56) References Cited

U.S. PATENT DOCUMENTS

| 5,628,230 | A | 5/1997 | Flam |
|---|---|---|---|
| 2002/0041724 | A1 | 4/2002 | Ronnekleiv et al. |
| 2018/0033339 | A1* | 2/2018 | Kerins .................. G09B 23/34 |

FOREIGN PATENT DOCUMENTS

| CN | 1895160 A | 1/2007 |
|---|---|---|
| CN | 101833891 A | 9/2010 |

(Continued)

OTHER PUBLICATIONS

Translation of CN 101912169A (Year: 2010).*

(Continued)

*Primary Examiner* — Chad H Smith
(74) *Attorney, Agent, or Firm* — Scully, Scott, Murphy & Presser, P.C.

(57) ABSTRACT

Disclosed are an intelligent bionic human body part model detection device and a method for manufacturing same. The device comprises: a bionic human body part model (1); and multiple optical fiber grating sensing units (5) which are integrated on an optical fibre and arranged at multiple pre-determined positions of the bionic human body part model (1). The device can improve the accuracy of the (Continued)

detection of pressure applied to the intelligent bionic human body part model.

10 Claims, 7 Drawing Sheets

(56) References Cited

FOREIGN PATENT DOCUMENTS

| | | | | |
|---|---|---|---|---|
| CN | 101912169 A | * | 12/2010 | |
| CN | 101912169 A | | 12/2010 | |
| CN | 101916319 A | | 12/2010 | |
| CN | 102184277 A | | 9/2011 | |
| CN | 103324907 A | | 9/2013 | |
| CN | 203203730 U | | 9/2013 | |
| CN | 103544733 A | | 1/2014 | |
| CN | 103761771 A | | 4/2014 | |
| CN | 104019759 A | | 9/2014 | |
| CN | 104036061 A | | 9/2014 | |
| CN | 104050856 A | | 9/2014 | |
| CN | 104392063 A | | 3/2015 | |
| CN | 204318732 U | | 5/2015 | |
| CN | 107154071 A | | 9/2017 | |
| CN | 107351102 A | * | 11/2017 | ............ B25J 13/084 |
| GB | 2466929 A | * | 7/2010 | ............ G01L 1/246 |
| JP | 2017-026348 A | | 2/2017 | |
| WO | WO 2016/119039 A1 | | 8/2016 | |

OTHER PUBLICATIONS

Translation of CN 107351102A (Year: 2017).*
Zhu Y. et al., "Fiber Grating, Metallization and Sensing Technology", pp. 5-7 (Apr. 30, 2016), together with an English-language translation.
Chinese Office Action dated Mar. 15, 2021 received in Chinese Application No. 201810249322.8, together with an English-language translation.
International Search Report dated Nov. 29, 2018 issued in PCT/CN2018/081017.

* cited by examiner

INTELLIGENT BIONIC HUMAN BODY PART MODEL DETECTION DEVICE AND METHOD FOR MANUFACTURING SAME

TECHNICAL FIELD

The present disclosure relates to the field of body pressure measurement, and in particular to an intelligent pressure sensing bionic human body part model device and a manufacturing method thereof.

BACKGROUND

The fit of clothing is very important for a pressure garment. The pressure garment forms suitable pressure on capillaries of human body and regulates blood circulation of the human body. Medical research shows that applying reasonable pressure can help prevent appearance of venous diseases (such as edema, phlebitis, thrombosis) and prevent further development of venous diseases. The pressure exerted by compression stockings on human legs largely depends on the localized leg shape and mechanical properties. In addition, the pressure garment or wearable devices can also be used to enhance exercise effects, reduce fatigue and injuries. Applying reasonable pressure is the key to positive effect of the pressure garment. Therefore, when manufacturing or applying the pressure garment, it is particularly important to accurately measure the pressure exerted on the human body. For example, in the design of compression stockings, pressure at the ankle should be maximized and gradually decrease along the leg. By squeezing blood vessels and muscles on the surface of the leg, part of the blood in these blood vessels is squeezed to other veins such as deeper veins, which helps more blood flow back to the heart and also reduces the amount of blood trapped in the legs.

The related methods for measuring pressure of the pressure garment on the human body can be divided into two categories according to whether it directly acts on the human body: a direct measurement type and an indirect measurement type. The measurement method of the direct measurement type may use pneumatic, piezoresistive, piezoelectric, capacitive sensors or sensor arrays to measure directly on the surface of the human body. These sensors or sensor arrays are large in size and located under the compression stockings, which will deform both the compression stockings and the legs, and it is impossible to measure true pressure exerted by the compression stockings on the human legs. In addition, the shape of the human legs changes slightly from morning to night. Therefore, the repeatability of these methods is very poor, and the measurement results are not accurate. The measurement method of indirect measurement type uses a human body part model to simulate a human body part, for example, using a human leg model to simulate a human leg. Then, electronic pressure sensors are set at different positions on the human body part model to measure the pressure applied by the compression stockings to the human body part model. However, the electronic pressure sensor has low detection signal accuracy, poor immunity to electromagnetic interference, slow measurement speed, poor reusability, small information capacity, large weight and volume, and is not durable. Moreover, the signal change of the electronic pressure sensor under an action of small pressure is not obvious, and its sensing response is the same order of magnitude as the noise generated by the environment or even smaller, so it is seriously interfered by external electromagnetic signals.

In addition, when constructing the human body part model, MST professional system in related arts uses a rigid human body part model. However, the pressure exerted by compression stockings on the human body is not uniform even in a cross-section with the same height, because the cross-sectional curvature varies with different positions, there are bone protrusions in some positions, and different tissues have different mechanical properties. In short, the related measurement methods may not accurately measure the pressure exerted by compression stockings on the human body, or may only measure the pressure between the compression stockings and the sensor embedded in the fixed and rigid human body part model, or the measured pressure is based on the assumption of an unreasonable cross-section. The measurement results of compression stockings do not match the actual pressure applied to the human leg, which will lead to excessive or insufficient pressure applied to the human body, causing discomfort to the user, failing to achieve the preset effect or even causing serious problems such as local ulceration.

In addition, there are obvious differences in human appearance. If considering differences in race, gender, age, etc., a large number of models of different sizes are required. Therefore, it is very worthwhile to build a deformable bionic model. The model has high measurement accuracy and can effectively reduce the difference between the test results of the pressure garment and the actual pressure applied to the human body.

SUMMARY

An object of the present disclosure is to provide a detection device of intelligent bionic human body part model capable of improving the accuracy of detecting applied pressure.

According to a first aspect of embodiments in the present disclosure, there is provided a detection device of intelligent bionic human body part model, including:
  a bionic human body part model; and
  a plurality of fiber grating sensing units integrated on an optical fiber and a plurality of predetermined positions set on the bionic human body part model.

In an embodiment, each of the plurality of fiber grating sensing units includes:
  a substrate;
  a groove on the substrate; and
  a Bragg grating, suspended on a surface of the groove, wherein an air chamber is formed at the groove after packaging.

In an embodiment, a plurality of optical fiber sensing channels are set on the bionic human body part model, the plurality of optical fiber grating sensing units are dispersed in each of the optical fiber sensing channels, at least one fiber grating sensing unit is dispersed in one fiber optic sensing channel, and at least one fiber grating sensing unit has different center wavelengths.

In an embodiment, material of the bionic human body part model is an elastomer with a Young's modulus below 1 MPa.

In an embodiment, the elastomer with a Young's modulus below 1 MPa is one or more of following:
  silicone, polyurethane, polyester, and polyacrylic acid.

In an embodiment, the detection device further includes:
  a base set at a bottom of the bionic human body part model;
  a protective layer integrally connected to an upper surface of the base for protecting the optical fiber.

In an embodiment, the bionic human body part model is generated as following: intercepting a plurality of cross-sections for each human body part sample among a plurality of human body part samples; selecting a plurality of parameters on each cross-section, the plurality of parameters uniquely defining the cross-section; constructing a parameter matrix using a plurality of parameters of a plurality of intercepted cross-sections for each human body part sample of the plurality of human body part samples; determining an average parameter matrix and a principal component vector for the parameter matrices of the plurality of human body part samples, wherein the average parameter matrix represents an average body part shape and the principal component vector represents a main difference of the human body part; and generating the bionic human body part model based on an average parameter matrix, a principal component vector, and at least one principal component measurement value on a target human body part.

According to a second aspect of embodiments in the present disclosure, there is also provided a method for manufacturing the above-mentioned detection device of intelligent bionic human body part model, including:
  intercepting a plurality of cross-sections for each human body part sample among a plurality of human body part samples;
  selecting a plurality of parameters on each cross-section, the plurality of parameters uniquely defining the cross-section;
  constructing a parameter matrix using a plurality of parameters of a plurality of intercepted cross-sections for each human body part sample of the plurality of human body part samples;
  determining an average parameter matrix and a principal component vector for the parameter matrices of the plurality of human body part samples, wherein the average parameter matrix represents an average body part shape and the principal component vector represents a main difference of the human body part; and
  generating the bionic human body part model based on the average parameter matrix, the principal component vector, and at least one principal component measurement value on a target human body part.

In an embodiment, the generating the bionic human body part model based on the average parameter matrix, the principal component vector, and at least one principal component measurement value on the target human body part, specifically includes:
  generating an average bionic human body part model based on the average parameter matrix; and
  deforming the average bionic human body part model according to at least one principal component measurement value on the target human body part and corresponding principal component value in the principal component vector.

In an embodiment, deforming the average bionic human body part model according to at least one principal component measurement value on the target human body part and corresponding principal component value in the principal component vector, specifically includes:
  determining a ratio of at least one principal component measurement value on the target human body part and the corresponding principal component value in the principal component vector; and
  deforming the average bionic human body part model according to product of the ratio and the principal component vector.

In an embodiment, before the generating the bionic human body part model based on the average parameter matrix, the principal component vector, and at least one principal component measurement value on the target human body part, the method further includes:
  obtaining a three-dimensional image of the target human body part; and
  obtaining at least one principal component measurement value on the target human body part from the three-dimensional image.

In an embodiment, the determining the principal component vector for the parameter matrices of the plurality of human body part samples specifically includes:
  obtaining the variance matrix for the parameter matrices of the multiple human body part samples; and
  determining the principal component vector based on the variance matrix.

In an embodiment, material used for generating the bionic human body part model includes an elastomer with a Young's modulus below 1 MPa.

In an embodiment, the elastomer with a Young's modulus below 1 MPa is one or more of following:
  silicone, polyurethane, polyester, and polyacrylic acid.

In an embodiment, after the generating the bionic human body part model based on an average parameter matrix, the method further includes: setting a plurality of fiber grating sensing units integrated on an optical fiber at a plurality of predetermined positions of the bionic human body part model.

In an embodiment, after the generating the bionic human body part model based on an average parameter matrix, the method further includes:
  setting a base at the bottom of the bionic human body part model; and
  integrally connecting a protective layer to an upper surface of the base for protecting the optical fiber.

In an embodiment, each of the plurality of fiber grating sensing units is constructed as follows:
  setting a substrate;
  etching a groove on the substrate; and
  suspending a Bragg grating on a surface of the groove, wherein an air chamber is formed at the groove after packaging.

In embodiments of the present disclosure, the fiber grating sensing unit is set at the plurality of predetermined positions on the bionic human body part model, instead of setting the electronic pressure sensor on the bionic human body part model, and these fiber grating sensing units are integrated on the optical fiber, that is, the fiber grating sensing network is adopted. The fiber grating sensor network has the following advantages: high measurement accuracy, strong anti-electromagnetic interference ability, fast measurement speed, good reusability, and large information capacity (one same fiber may transmit multiple signals). In addition, the fiber grating sensing unit also has characteristics of light weight, small size, insulation, durability, long-term stability and so on. Moreover, sensing of each fiber grating sensing unit is independent of each other, and mutual interference is very small, which can effectively inhibit/isolate the transmission of internal fiber deformation and external fiber deformation of the fiber grating sensing unit. In related art, an electronic pressure sensor is applied to the bionic human body part model, the signal generated under small pressure does not change significantly, and its sensing response is the same order of magnitude as the noise generated by the environment or even smaller, so it is seriously interfered by external signals. The embodiments of the present disclosure adopt the fiber grating sensor network, which can effectively avoid the problem.

Other characteristics and advantages of the present disclosure will become apparent through the following detailed description, or partly learned through the practice of the present disclosure.

It should be understood that the above general description and the following detailed description are merely exemplary, which are not limited to the present disclosure.

BRIEF DESCRIPTION OF THE DRAWINGS

Exemplary embodiments of the present disclosure will be described in detail below with reference to accompanying drawings, the above and other objects, features, and advantages of the present disclosure can become more apparent.

DETAILED DESCRIPTION

Exemplary embodiments of the present disclosure will now be described more fully with reference to accompanying drawings. However, the exemplary embodiments herein are provided to assist in the understanding of the disclosure and are not intended to limit the disclosure in any way. On the contrary, the embodiments are provided to make the description of the present disclosure more comprehensive and complete, and to transmit the concept of the exemplary embodiments to those skilled in the art. The drawings are only schematic representations of the disclosure, and are not necessarily to scale. The same reference numerals in the drawings denote the same or similar parts, and the repeated description thereof will be omitted.

Further, described features, structures, or advantages can be combined in any suitable manner in one or more embodiments. In the following description, numerous specific details are provided to give a full understanding of the embodiments of the present disclosure. However, one skilled in the art may appreciate that one or more of the specific details can be omitted while practicing technical solutions of the present disclosure, or using other equivalent methods, methods, apparatuses and steps to substitute. In other cases, well-known structures, methods, implementations, or operations are not shown or described in detail to avoid overwhelming attention and obscure various aspects of the present disclosure.

Some of block diagrams shown in the drawings are functional entities and do not necessarily correspond to physically or logically independent entities. These functional entities can be implemented in the form of software, or implemented in one or more hardware modules or integrated circuits, or implemented in different networks and/or processor devices and/or microcontroller devices.

Figure 6:
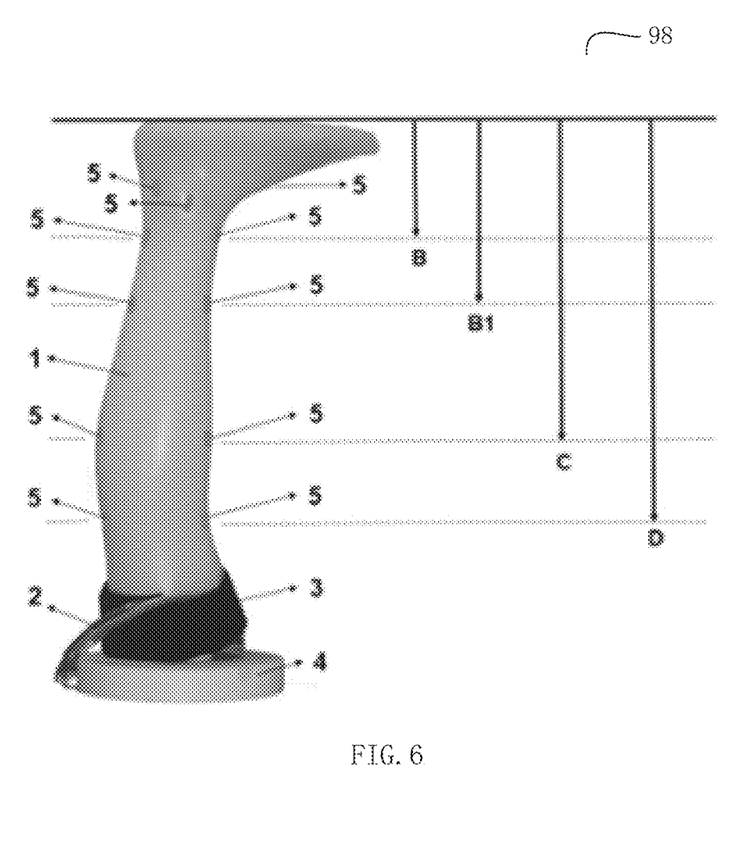
FIG. 6 is a structural diagram of a detection device of intelligent bionic human body part model according to an exemplary embodiment of the present disclosure.

FIG. 6 is a structural diagram of a detection device of intelligent bionic human body part model according to an exemplary embodiment of the present disclosure.

The body part refers to the part on the human body that is in contact with the pressure garment. For example, for pressure stockings, the body parts that are in touched contact with the pressure stockings are the legs. The bionic human body part model refers to a bionic model of the human body part used in order to detect pressure generated by the pressure garment on the human body part when the pressure garment is manufactured. The detection device of intelligent bionic human body part model is a complete device that uses the bionic human body part model to detect the pressure generated by the pressure garment on the human body part, including the bionic human body part model and other supporting units such as a detection unit used to detect the pressure generated by the pressure garment on the human body part. Intelligence means that the bionic human body part model may monitor pressure distribution in real time, and may deform based on different human bodies.

As shown in FIG. 6, the detection device of intelligent bionic human body part model includes:
 a bionic human body part model 1; and
 a plurality of fiber grating sensing units 5 integrated on an optical fiber 2 and a plurality of predetermined positions set on the bionic human body part model 1.

The predetermined positions refer to preset positions on the bionic human body part model to measure the pressure generated by the pressure garment on the bionic human body part model, and can be predefined by an operator. As shown in FIG. 6, the plurality of fiber grating sensing units 5 are set at the plurality of predetermined positions on the bionic human body part model 1 of the detection device 98 of intelligent bionic human body part model. Each optical fiber 2 is connected to the plurality of fiber grating sensing units 5.

The principle of the fiber grating sensing unit for sensing pressure is: taking Bragg fiber grating sensing as an example, when light passes through the fiber grating, the fiber grating will reflect or transmit a narrow spectrum component with a specific wavelength as a center wavelength. At the same time, external physical parameters (such as temperature, strain, etc.) may cause wavelength shift.

For each fiber grating sensing unit, the pressure acting on the surface can be transferred and converted into stretching of the fiber grating. At the same time, the relationship between the pressure/strain and the center wavelength of a reflected signal of the fiber grating is established. Applying the relationship, the pressure measurement can be performed by the fiber grating sensing unit.

In embodiments of the present disclosure, the fiber grating sensing unit is set at the plurality of predetermined positions on the bionic human body part model, instead of setting the electronic pressure sensor on the bionic human body part model, and these fiber grating sensing units are integrated on the optical fiber, that is, the fiber grating sensing network is adopted. The fiber grating sensor network has the following advantages: high measurement accuracy, strong anti-electromagnetic interference ability, fast measurement speed, good reusability and large information capacity (one same fiber may transmit multiple signals). In addition, the fiber grating sensing unit also has characteristics of light weight, small size, insulation, durability, long-term stability and so on. Moreover, sensing of each fiber grating sensing unit is independent of each other, and mutual interference is very small, which can effectively inhibit/isolate the transmission of internal fiber deformation and external fiber deformation of the fiber grating sensing unit. In related art, an electronic pressure sensor is applied to the bionic human body part model, the signal generated under small pressure does not change significantly, and its sensing response is the same order of magnitude as the noise generated by the environment or even smaller, so it is seriously interfered by external signals. The embodiments of the present disclosure adopt the fiber grating sensor network, which can effectively avoid the problem.

Figure 7:
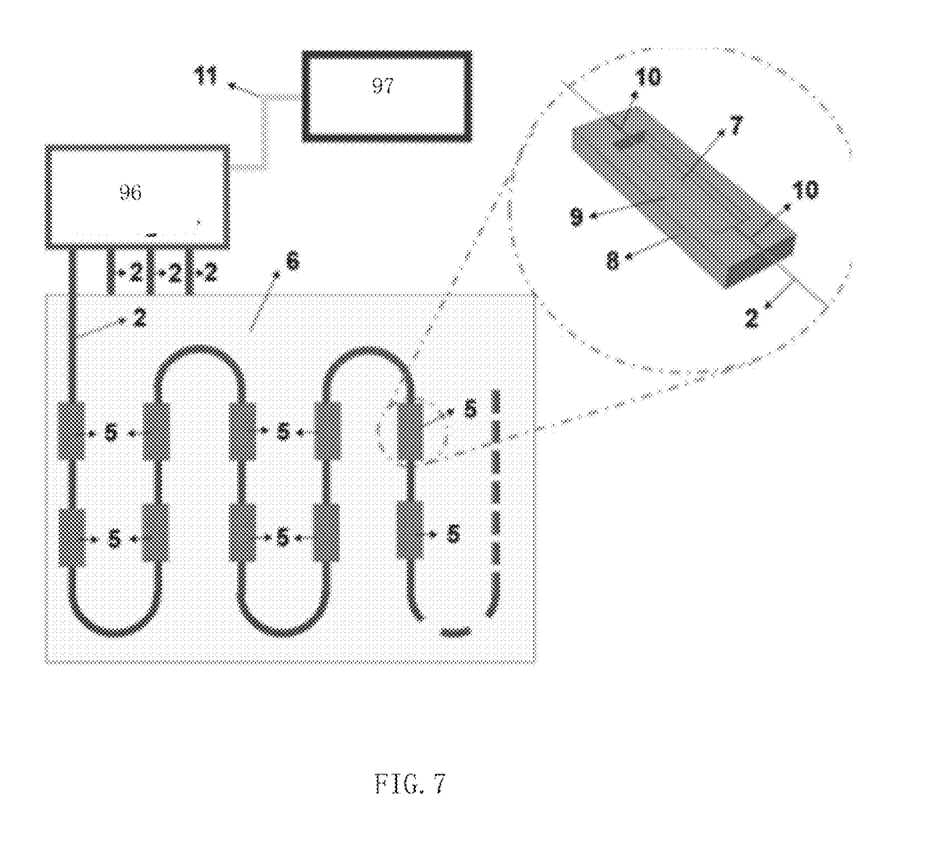
FIG. 7 is an exemplary structure of a part of the detection device of intelligent bionic human body part model except for the bionic human body part model according to an exemplary embodiment of the present disclosure.

In an embodiment, as shown in FIG. 7, each of the plurality of fiber grating sensing units 5 includes:
a substrate 8;
a groove 9 on the substrate 8; and
a Bragg grating 7, suspended on a surface of the groove 9, wherein an air chamber is formed at the groove after packaging.

The advantage of using Bragg grating to fabricate fiber grating sensing unit is that it can be free from electromagnetic interference and has high sensitivity to axial stretch.

Since the air chamber is formed at the groove of the above structure after packaging, it is also very easy to deform under small pressure, thus showing a very high sensitivity (At present, the pressure sensitivity in the range of 0-10 kPa is higher than 20 pm/kPa, and the pressure and wavelength shift are linear).

In an embodiment, a plurality of optical fiber sensing channels are set on the bionic human body part model 1, the plurality of optical fiber grating sensing units are dispersed in each of the optical fiber sensing channels, at least one fiber grating sensing unit is dispersed in one fiber optic sensing channel, and at least one fiber grating sensing unit has different center wavelengths. For example, 4 fiber grating sensor channels are set on the bionic human body part model 1, and each channel has 7 fiber grating sensing units, and the center wavelengths of the gratings of these 7 fiber grating sensing units are different from each other. For example, each fiber grating sensor channel is a fiber branch, and a plurality of fiber branches are juxtaposed to form a unified fiber.

The above structure utilizes the principle of wavelength division multiplexing, and uses fiber grating sensing units with different central wavelengths in each optical fiber sensing channel to measure the pressure distribution caused by garment on the bionic human body part model. In each channel, a broad-spectrum light source provides an input signal, through fiber gratings with different center wavelengths integrated in one same fiber, and each fiber grating reflects a narrow-band spectrum with different center wavelengths.

In an embodiment, material used for manufacturing the constructed bionic human body part model includes an elastomer with a Young's modulus below 1 MPa. The advantage of using the elastomer with a Young's modulus below 1 MPa is that it is similar to a Young's modulus of skin, and it has better elastic recovery performance and shape retention, convenient processing, and reasonable cost.

In an embodiment, the elastomer with a Young's modulus below 1 MPa is one or more of following: silicone, polyurethane, polyester, and polyacrylic acid.

In an embodiment, the detection device further includes:
a base 4 set at a bottom of the bionic human body part model 1;
a protective layer 4 integrally connected to an upper surface of the base 4 for protecting the optical fiber.

As shown in FIG. 6, the base 4 is at the bottom of the bionic human body part model 1, which can improve stability and facilitate measurement. The protective layer 3 is integrally connected to the base 4 to protect the optical fiber 2. Such a structure can make the detection device 98 of intelligent bionic human body part model not easily damaged.

In an embodiment, as shown in FIG. 7, a plurality of fiber grating sensing units 5 are embedded in a soft elastic body 6 without protruding from the soft elastic body 6. The soft elastic body 6 is set on the bionic human body part model.

The advantage of embedding the fiber grating sensing units 5 with the Bragg grating 7 in the elastic body 6 is that the elastic body 6 is soft and flexible, and the elastic coefficient of the optical fiber is 2-3 orders of magnitude larger than that of the elastic body 6, so that the axial deformation of the optical fiber under pressure is very small, and the sensitivity under small pressure is relatively low. The fiber grating pressure sensing units shown in FIG. 7 can just solve this problem.

In an embodiment, an interrogator 96 (for example, a light sensor interrogator) detects that the fiber grating sensing units 5 output a detection result, and sends the detection result to a processor 97 via Ethernet 11 for the processor to process the pressure on the detected human body part model to obtain the detection result.

In an embodiment, the optical fiber 2 is straight and fixed to the substrate 8 by an adhesive 10 to increase pretension.

In an embodiment, the substrate 8 is a hard substrate, and its elastic coefficient is similar to that of the optical fiber 2.

Since a detection unit of optical fiber pressure adopts the above structure, the cross section is larger, and rigidity of the substrate 8 is much higher than that of the optical fiber 2. In this way, the hard substrate that produces negligible deformation under the action of the pressure garment can avoid the interference of the connected optical fiber, and effectively limit the interference between different detection units of optical fiber pressure connected to the same fiber. In addition, the advantage of the groove is that air can be contained in the groove, which is advantageous for improving the pressure sensitivity. Based on the above design, there is a linear relationship between the wavelength drift of the Bragg grating and the pressure of the bionic human body part model, which improves repeatability of detection and reduces hysteresis. The sensitivity of the detection units of optical fiber pressure in the embodiments of the present disclosure can reach 20 pm/kpa.

Figure 1:
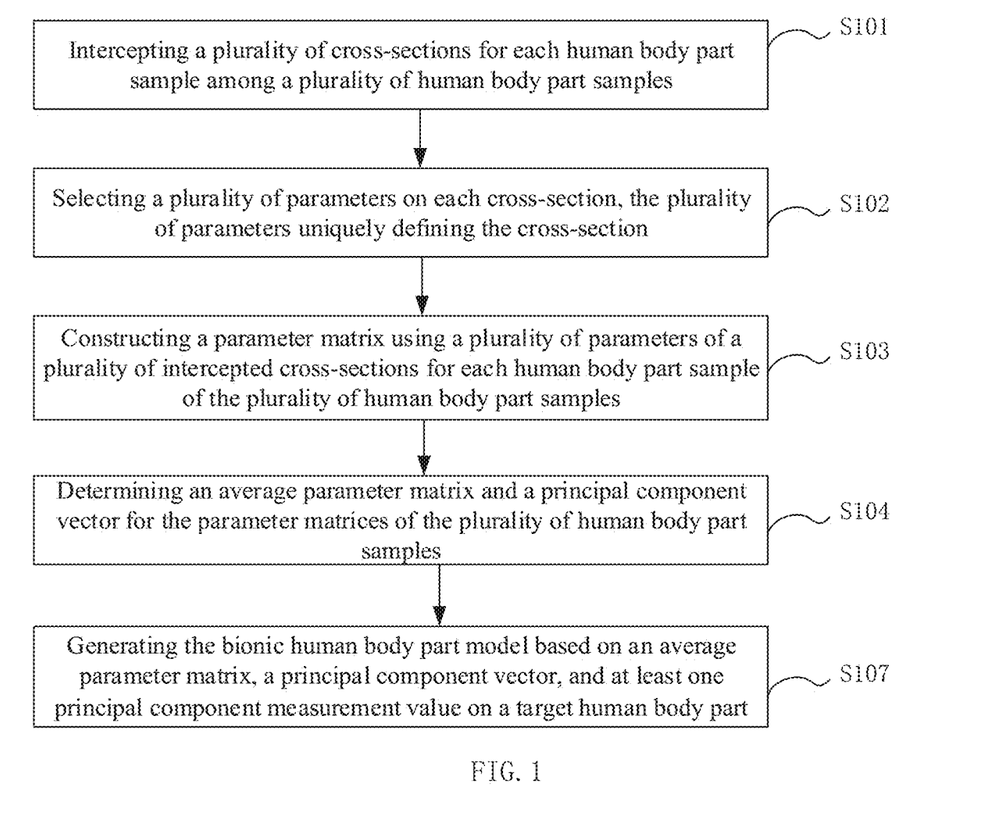
FIG. 1 is a flowchart of a method for manufacturing a detection device of intelligent bionic human body part model detection device according to an exemplary embodiment of the present disclosure.

As shown in FIG. 1, in an embodiment, the bionic human body part model is generated as following:

In step S101, a plurality of cross-sections are intercepted for each human body part sample among a plurality of human body part samples;

In step S102, a plurality of parameters are selected a on each cross-section, wherein the plurality of parameters uniquely defines the cross-section;

In step S103, a parameter matrix is constructed using a plurality of parameters of a plurality of intercepted cross-sections for each human body part sample of the plurality of human body part samples;

In step S104, an average parameter matrix and a principal component vector are calculated for the parameter matrices of the plurality of human body part samples, wherein the average parameter matrix represents an average body part shape and the principal component vector represents a main difference of the human body part; and In step S107, the bionic human body part model is generated based on the average parameter matrix, the principal component vector, and at least one principal component measurement value on a target human body part.

These steps are described in detail below.

In step S101, a plurality of cross-sections are intercepted for each human body part sample among a plurality of human body part samples.

Human body parts refer to parts on the human body, such as human legs. The human body part samples refer to the human body parts selected in advance for testing in order to obtain an average human body part model and principal component vector. The concept of the average human body part model and the principal component vector will be described later. The more samples are selected, the more accurate the test result is. For example, the test result of selecting 1000 human legs as a sample is more accurate than the test result of selecting 100 legs as a sample.

Figure 8:
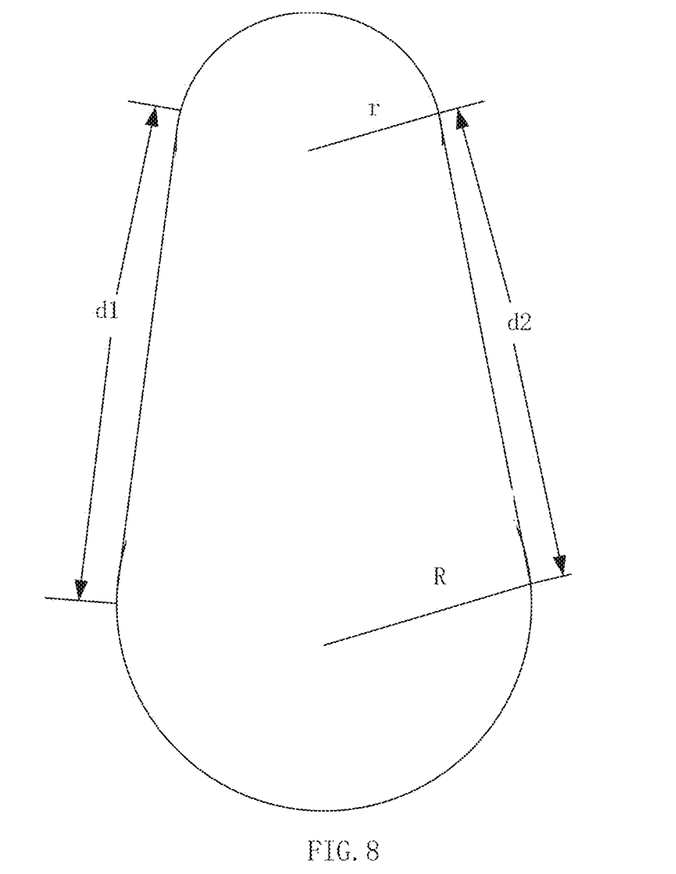
FIG. 8 is a schematic diagram of selecting a parameter uniquely defining the cross-section in a cross-section of a human leg in according to an exemplary embodiment of the present disclosure.

For each sample, the plurality of cross-sections are intercepted. For example, a cross-section is intercepted every 0.05 meters in the height direction of the leg, and the cross-section intercepted is shown in FIG. 8. The more cross-sections are intercepted, the more accurate the measurement result is.

In step S102, a plurality of parameters are selected a on each cross-section, wherein the plurality of parameters uniquely defines the cross-section.

Parameters refer to variables that need to be used in order to characterize the whole or part of the cross-sectional profile shape. In an embodiment, the cross-section of the human leg is shown in FIG. 8. The cross-section of the human leg is seen as a small circle arc and a large circle arc connected by two straight tangent lines. After the radius r of the small circle, the radius R of the large circle, and lengths d1 and d2 of the two straight tangent lines are determined, the cross-sectional profile shape is uniquely determined. As long as one of these four variables is uncertain, the profile shape of the cross-section is uncertain. The radius r of the small circle, the radius R of the large circle, and the lengths d1 and d2 of the two straight tangent lines are selected parameters, which can uniquely define the cross-section.

In step S103, a parameter matrix is constructed using a plurality of parameters of a plurality of intercepted cross-sections for each human body part sample of the plurality of human body part samples.

The parameter matrix refers to a matrix composed of the plurality of parameters of the plurality of intercepted cross-sections for the human body part sample, wherein one of row and column of the matrix represents the cross-section, the other represents the parameter, and elements of the matrix represent corresponding parameter values of corresponding cross-section. For example, the row represents the cross-section, and the column represents the parameter. The radius r of the small circle, the radius R of the large circle, and the lengths d1 and d2 of the two straight tangent lines are represented by columns 1-4, respectively, and the element represents the radius R of the large circle of the third cross-section.

In step S104, an average parameter matrix and a principal component vector are calculated for the parameter matrices of the plurality of human body part samples.

The average parameter matrix refers to a matrix obtained by averaging the plurality of parameter matrices. Averaging the plurality of parameter matrices refers to performing such operations on the plurality of parameter matrices: averaging the parameters at the same position (the row number and column number are the same) of the plurality of parameter matrices as the parameter at the same position of the average parameter matrix. The average parameter matrix represents a level of each parameter on each cross-section of an average human body part. Taking the element in the third row and the second column above that represents the radius R of the third cross-section of the large circle as an example, the element in the third row and the second column of the average parameter matrix represents the average level of the radius R of the large circle of the third cross-section of the human body part of a large number of people.

The principal component vector refers to a vector composed of variance that is obtained by performing principal component analysis on the parameter matrix of the plurality of human body parts samples, extracting the most significant parameters of different people in the parameter matrix and calculating the variance. The principal component analysis is a commonly used method in the field, it can extract the most significant element composition. For example, the element in the third row and the first column of the parameter matrix of the plurality of human body part samples have very little difference among different people, and the element in the third row and the second column of the parameter matrix of the plurality of human body part samples vary greatly among different people. This means that in different people, the radius r of the small circle of the third cross-section of the human body has very little difference, the radius R of the large circle of the third cross-section of the human body is very different, and the effect of using it to distinguish different human body parts is obvious. At this time, the variances of the element in the third row and second column of the parameter matrix of the plurality of human body part samples are put into the principal component vector as the principal component.

In an embodiment, the determining the principal component vector for the parameter matrices of the plurality of human body part samples specifically includes the following steps.

The variance matrix for the parameter matrices of the multiple human body part samples is obtained; and The principal component vector is determined based on the variance matrix.

The variance matrix refers to a matrix obtained by calculating the variance of the plurality of parameter matrices. Calculating the variance of the plurality of parameter matrices refers to performing such operations on the plurality of parameter matrices: calculating the variance of the parameters at the same position (the row number and column number are the same) of the plurality of parameter matrices as the parameter at the same position of the variance matrix. The variance at a specific position of the variance matrix indicates the degree of difference among different people in the parameters of the cross-section of the human body part corresponding to the specific position. The larger the variance at the specific position is, the larger the difference in the parameters of the corresponding cross-section of human body part among different people is. Therefore, the element (variance) with the larger value in the variance matrix is extracted to synthesis the principal component vector. Each principal component in the principal component vector is the variance extracted from the position with the larger variance in the variance matrix. The position where the variance is relatively large is the parameter with relatively large difference in the corresponding parameter in the human body.

In step S107, the bionic human body part model is generated based on an average parameter matrix, a principal component vector, and at least one principal component measurement value on a target human body part.

The target human body part refers to the human body part for which the bionic human body part model is to be generated. For example, a user wants to order stockings. After the stockings leave the factory, it is not known whether the stockings are suitable for the user. Therefore, it is necessary to generate a bionic leg model for the user's leg, which is very close to the shape of the user's leg. The stockings are worn on the bionic leg model, and it can be checked whether the stockings are suitable for the user through the pressure sensor on the bionic leg model. At this time, the user's leg is the target body part.

The principal component measurement value on the target human body part refers to the difference between the value obtained by measuring the parameter with the most significant difference among different people in the target human body part and the average value of the parameter. The average value of the parameter refers to the parameter value at the position of the parameter in the average parameter matrix. For example, the principal component vector includes the variance of the radius R of the large circle of the third cross-section, the variance of the radius r of the small circle of the fifth cross-section, and the variance of the radius r of the small circle of the seventh cross-section. Assuming that the variance of the radius R of the large circle of the third cross-section is 4 cm, and the average value of the radius R of the large circle of the third cross section is 5 cm, the radius R of the large circle of the third cross-section of the target human leg is measured to be 7 cm, then the principal component measurement value of the radius R of the large circle corresponding to the third cross-section of the target leg is 7−5=2 (cm).

Figure 2:
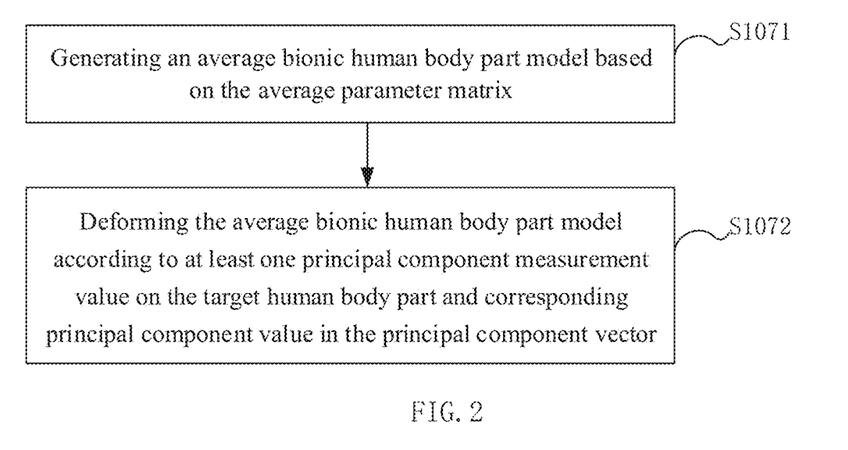
FIG. 2 is a specific flowchart of generating the bionic human body part model based on an average parameter matrix, a principal component vector, and at least one principal component measurement value on a target human body part according to an exemplary embodiment of the present disclosure.

As is shown in FIG. 2, in an embodiment, the step S107 specifically includes the following steps.

S1071: an average bionic human body part model based on the average parameter matrix is generated; and S1072: the average bionic human body part model is deformed according to at least one principal component measurement value on the target human body part and corresponding principal component value in the principal component vector.

Since the average parameter matrix represents, for one average human body part, the level of each parameter on each cross-section, according to each parameter in the matrix, an average bionic human body part model can be generated, which represents the shape of the average human body part among all people. For example, according to the average level of each parameter on each cross-section of the human leg, an average human leg model can be constructed, that is, the average bionic human body part model, which reflects the average human leg shape. 3D printing technology can be used to generate the average bionic human body part model.

Figure 3:
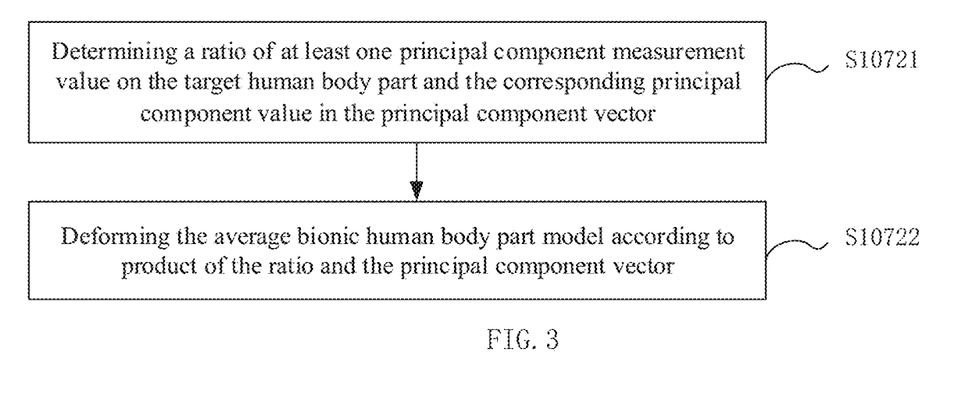
FIG. 3 is a specific flowchart of deforming the average bionic human body part model according to at least one principal component measurement value on the target human body part and corresponding principal component value in the principal component vector according to an exemplary embodiment of the present disclosure.

In an embodiment, as is shown in FIG. 3, the step S1072 specifically includes the following steps.

S10721: a ratio of at least one principal component measurement value on the target human body part and the corresponding principal component value in the principal component vector is determined; and S10722: the average bionic human body part model is deformed according to product of the ratio and the principal component vector.

The ratio of at least one principal component measurement value on the target human body part and the corresponding principal component value in the principal component vector represents that, for the parameter corresponding to the at least one principal component measurement value, the degree to which the value of the parameter of the target human body part deviates from the average level of the parameter value (that is, the parameter value of the corresponding position in the average parameter matrix) in the entire population distribution. The higher the ratio is, the more severe the deviation of the parameter of the target human body part from the average level in the entire population distribution is. For example, the probability that the deviation from the mean is less than or equal to the variance is 68.5%, that is, 68.5% of people's parameter value will fall within the interval of (mean−variance, mean+variance). If the ratio of at least one principal component measurement value on the target human body part to the corresponding principal component value in the principal component vector is 3, then 99% of people's parameter value will fall within (mean−3 times the variance, mean+3 times the variance), indicating that the value of this parameter is far from the average level of this parameter.

Since each human body part is proportional, the ratio of at least one principal component measurement value on the target human body part and the corresponding principal component value in the principal component vector also represents the ratio of other principal component measurement values on the target human body part to the corresponding principal component values in the principal component vector.

For example, the principal component vector has the radius R of the large circle of the third cross-section, the radius r of the small circle of the fifth cross-section, and the radius r of the small circle of the seventh cross-section. The average value of the radius R of the large circle of the third cross-section is 5 cm, and the variance is 2 cm. The radius R of the large circle of the third cross-section on the leg of the target user is measured to be 6 cm. The ratio of the measurement value of the principal component corresponding to the radius R of the large circle of the third cross-section on the user's leg to the corresponding principal component value in the principal component vector is (6−5)/2=0.5. The average value of the radius r of the small circle of the fifth cross-section is 3 cm, and the variance is 1 cm. The product of the ratio of 0.5 and the variance of 1 cm of the radius r of the small circle of the fifth cross-section is 0.5 cm, then the radius r of the small circle of the fifth cross-section of the average bionic human body part model is deformed according to 0.5 cm. The average value of the radius r of the small circle of the seventh cross-section is 2 cm, and the variance is 0.4 cm. The product of the ratio of 0.5 and the radius of the small circle of the seventh cross-section r and the variance of 0.4 cm is 0.2 cm, then the radius r of the small circle of the seventh cross-section of the average bionic human body part model is deformed according to 0.2 cm.

The way of deformation can be carried out by inflating or deflating the average bionic human body part model, etc., or can be other mechanical driving methods, or can be carried out by other methods known to those skilled in the art.

Figure 4:
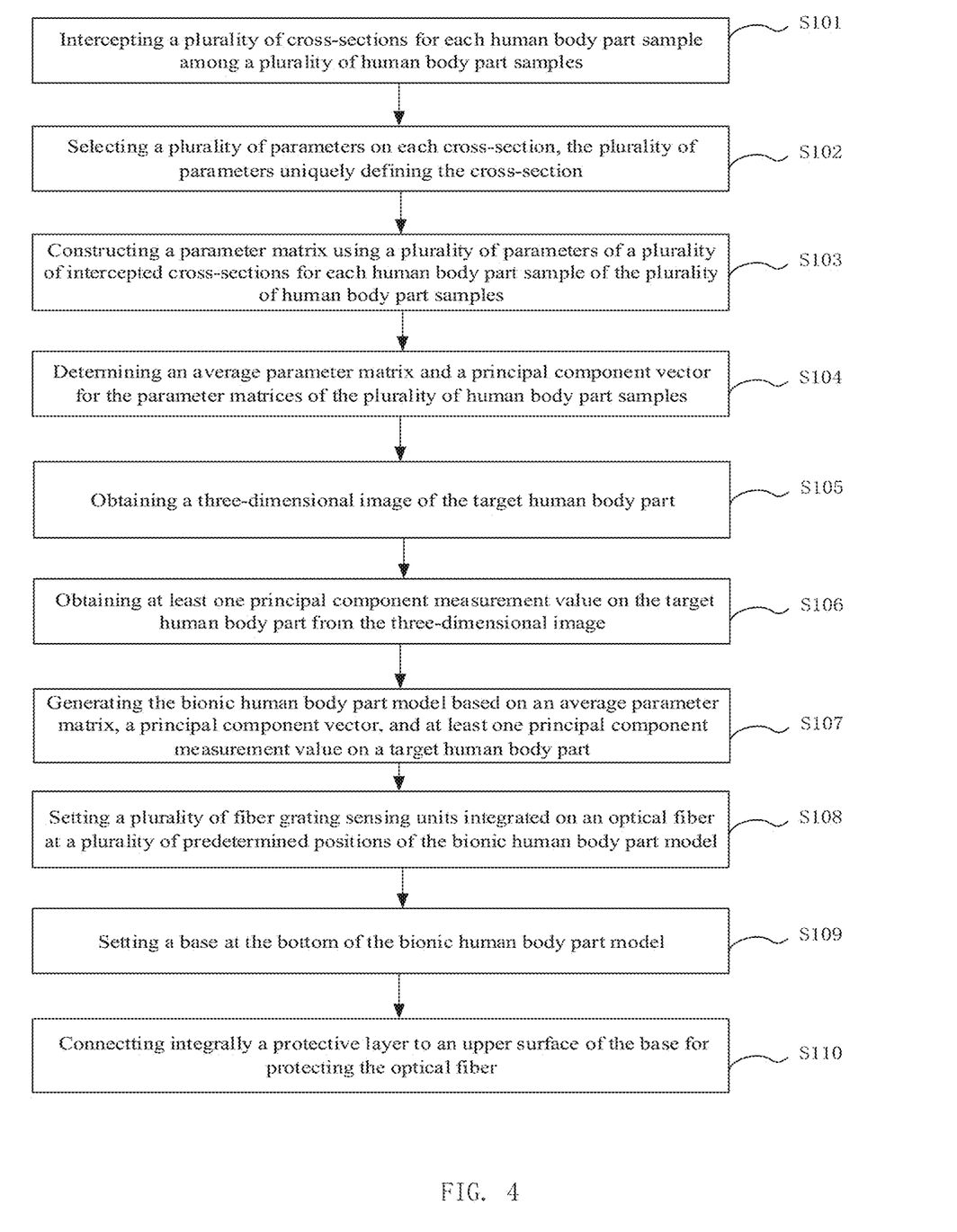
FIG. 4 is a flowchart of a method for manufacturing a detection device of intelligent bionic human body part model detection device according to an exemplary embodiment of the present disclosure.

As shown in FIG. 4, in an embodiment, before step S107, the method further includes the following steps.

S105: a three-dimensional image of the target human body part is obtained; and

S105: at least one principal component measurement value on the target human body part is obtained from the three-dimensional image.

The three-dimensional image of the human body part refers to an image of the human body part that extends in three dimensions (for example, x-axis, y-axis, and z-axis) in a three-dimensional coordinate system.

In an embodiment, step S105 can be implemented by 3D scanning.

In step S106, since the three-dimensional image of the target human body part is obtained, at least one principal component measurement value on the target human body part can be obtained in the three-dimensional image. For example, from the captured three-dimensional image of the user's human leg, it can be obtained that the radius R of the large circle of the third cross-section of the human leg minus the average value of the radius R of the great circle of the third cross-section is the corresponding principal component measurement value.

In the embodiments of the present disclosure, instead of simply defining human body parts (such as human legs) through simple measurement values (such as thigh length, calf length, knee diameter, and foot length), the plurality of cross-sections of human body parts (such as different heights of cross-sections of legs) are intercepted, the plurality of parameters are selected on each cross-section to uniquely define the cross-section (for example, the cross-section of the leg is regarded as a small circle arc and a large circle arc connected by two straight tangent lines, and the radius of the small circle, the radius of the large circle, and the length of each of the two straight tangent lines may uniquely define the cross-section). In this way, the various parameters selected on each cross-section are combined to form the parameter matrix. Compared with the simple measurement values (such as thigh length, calf length, knee diameter, and foot length) of the related art, the matrix may more effectively capture and represent the shape details of human body parts. The average parameter matrix and the principal component vector for the parameter matrix of a large number of human body part samples are calculated in the embodiments of the present disclosure, where the average parameter matrix represents the average body part shape, and the principal component vector represents the main difference of the human body part. In this way, the average parameter matrix corresponds to an average human body part (each parameter of each cross-section of the human body part takes the average value of the corresponding parameter of the corresponding cross-section of the large number of human body part samples). Through the principal component vector, it can be known that which parameters are dominant among all the parameters of all cross-sections of the human body part, which can reflect the differences of different people and the level of change between different people for the parameter. Then, according to at least one principal component measurement value on the target human body part, it can be known that the position of the target human body part of the target person in all the population in terms of the principal component, and then it can be known that how much deformation of the average human body part model corresponding to the average parameter matrix can be made to be close to the real shape of the target human body part. Therefore, the detection device of intelligent bionic human body part model manufactured by this method is more accurate in detecting the pressure of the pressure garment on the human body part, and reduces the pressure measurement result of the pressure garment on the human leg. And the difference between the real pressure generated by pressure garment on human legs.

As shown in FIG. 4, in one embodiment, the method further includes step S108, a plurality of fiber grating sensing units integrated on an optical fiber are set at a plurality of predetermined positions of the bionic human body part model.

As shown in FIG. 4, in an embodiment, the method further includes the following steps.

In step S109, a base at the bottom of the bionic human body part model is set; and In step S110, a protective layer to an upper surface of the base for protecting the optical fiber is integrally connected.

Figure 5:
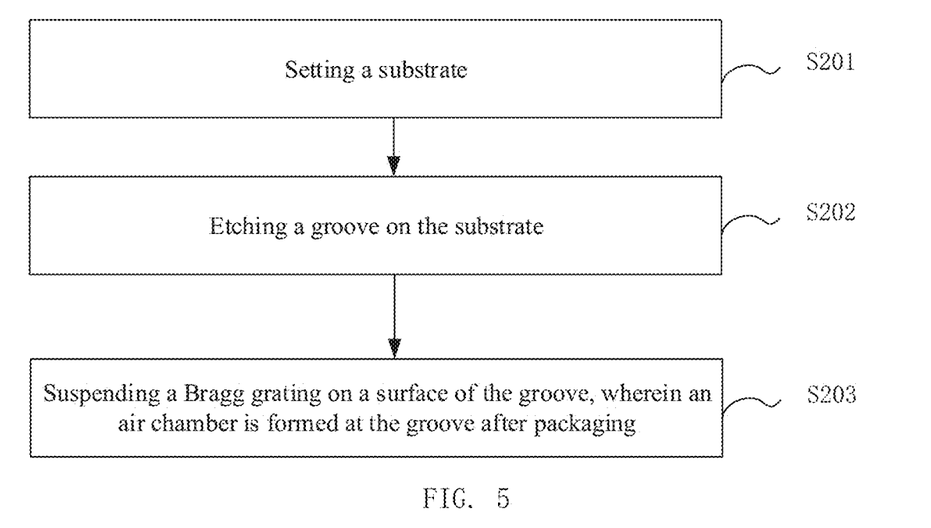
FIG. 5 is a specific flowchart of a method for constructing a fiber grating sensing unit according to an exemplary embodiment of the present disclosure.

As shown in FIG. 5, in an embodiment, each of the plurality of fiber grating sensing units is constructed as follows:

In step S201, a substrate is set;

In step S202, a groove on the substrate is etched; and

In step S203, a Bragg grating on a surface of the groove is suspended, wherein an air chamber is formed at the groove after packaging.

Those skilled in the art will easily think of other embodiments of the present disclosure after considering the specification and practicing the invention disclosed herein. The present disclosure is intended to cover any variations, uses, or adaptive changes of the present disclosure. These variations, uses, or adaptive changes follow the general principles of the present disclosure and include common knowledge or conventional technical means in the technical field not disclosed in the present disclosure. The description and the embodiments are to be regarded as exemplary only, and the true scope and spirit of the present disclosure are pointed out by the following claims.

It should be understood that the present disclosure is not limited to the precise structure that has been described above and shown in the drawings, and various modifications and changes can be made without departing from its scope. The scope of the present disclosure is limited only by the appended claims.

What is claimed is:

1. A method for manufacturing a detection device of intelligent bionic human body part model, the detection device of intelligent bionic human body part model comprising:

a bionic human body part model; and a plurality of fiber grating sensing units integrated on an optical fiber and a plurality of predetermined positions set on the bionic human body part model, wherein the method comprises:

intercepting a plurality of cross-sections for each human body part sample among a plurality of human body part samples;

selecting a plurality of parameters on each cross-section, the plurality of parameters uniquely defining the cross-section;

constructing a parameter matrix using a plurality of parameters of a plurality of intercepted cross-sections for each human body part sample of the plurality of human body part samples;

determining an average parameter matrix and a principal component vector for the parameter matrices of the plurality of human body part samples, wherein the average parameter matrix represents an average body part shape and the principal component vector represents a main difference of the human body part; and generating the bionic human body part model based on an average parameter matrix, a principal component vector, and at least one principal component measurement value on a target human body part.

2. The method according to claim 1, wherein the generating the bionic human body part model based on the average parameter matrix, the principal component vector, and at least one principal component measurement value on the target human body part, specifically comprises:

generating an average bionic human body part model based on the average parameter matrix; and deforming the average bionic human body part model according to at least one principal component measurement value on the target human body part and corresponding principal component value in the principal component vector.

3. The method according to claim 2, wherein the deforming the average bionic human body part model according to at least one principal component measurement value on the target human body part and corresponding principal component value in the principal component vector, specifically comprises:

determining a ratio of at least one principal component measurement value on the target human body part and the corresponding principal component value in the principal component vector; and deforming the average bionic human body part model according to product of the ratio and the principal component vector.

4. The method according to claim 1, wherein before the generating the bionic human body part model based on the average parameter matrix, the principal component vector, and at least one principal component measurement value on the target human body part, the method further comprises:

obtaining a three-dimensional image of the target human body part; and obtaining at least one principal component measurement value on the target human body part from the three-dimensional image.

5. The method according to claim 1, wherein the determining the principal component vector for the parameter matrices of the plurality of human body part samples specifically comprises:

obtaining the variance matrix for the parameter matrices of the multiple human body part samples; and determining the principal component vector based on the variance matrix.

6. The method according to claim 1, wherein material used for generating the bionic human body part model comprises an elastomer with a Young's modulus below 1 MPa.

7. The method according to claim 6, wherein the elastomer with a Young's modulus below 1 MPa is one or more of following:

silicone, polyurethane, polyester, and polyacrylic acid.

8. The method according to claim 1, wherein after the generating the bionic human body part model based on an average parameter matrix, the method further comprises:

setting a plurality of fiber grating sensing units integrated on an optical fiber at a plurality of predetermined positions of the bionic human body part model.

9. The method according to claim 1, wherein after the generating the bionic human body part model based on an average parameter matrix, the method further comprises:

setting a base at the bottom of the bionic human body part model; and integrally connecting a protective layer to an upper surface of the base for protecting the optical fiber.

10. The method according to claim 1, wherein each of the plurality of fiber grating sensing units is constructed as follows:

setting a substrate;

etching a groove on the substrate; and suspending a Bragg grating on a surface of the groove, wherein an air chamber is formed at the groove after packaging.

* * * * *